United States Patent [19]
McCullough

[11] Patent Number: 6,139,828
[45] Date of Patent: Oct. 31, 2000

[54] HAIR CARE FORMULATIONS

[75] Inventor: John E. McCullough, Indianapolis, Ind.

[73] Assignee: Hair Associates, LLC, Carmel, Ind.

[21] Appl. No.: 09/324,283

[22] Filed: Jun. 2, 1999

[51] Int. Cl.[7] .............................. A61K 7/075; A61K 7/08
[52] U.S. Cl. ...................................... 424/70.24; 424/195.1
[58] Field of Search .................................. 424/70.24, 74, 424/195.1

[56] References Cited

U.S. PATENT DOCUMENTS

| | | | |
|---|---|---|---|
| 4,358,286 | 11/1982 | Grollier et al. | 424/74 |
| 4,839,168 | 6/1989 | Abe et al. | 424/74 |
| 5,610,071 | 3/1997 | Sabal . | |
| 5,869,063 | 2/1999 | Lezdey et al. | 424/195.1 |
| 5,916,565 | 6/1999 | Rose et al. | 424/195.1 |
| 5,925,615 | 7/1999 | Kern et al. | 510/463 |

FOREIGN PATENT DOCUMENTS

WO 99/21006  4/1999  WIPO .

*Primary Examiner*—Thurman K. Page
*Assistant Examiner*—Liliana Di Nola-Baron
*Attorney, Agent, or Firm*—Mary Ann Tucker

[57] ABSTRACT

Hair care formulations for cleansing the scalp and hair follicle openings are disclosed which comprises black cohosh extract, and a surfactant selected from the group consisting of sodium $C_{14-16}$ olefin sulfonate, sodium lauryl sulfoacetate, disodium laureth sulfosuccinate and combinations thereof

14 Claims, No Drawings

HAIR CARE FORMULATIONS

BACKGROUND OF THE INVENTION

The present invention relates to formulations useful as hair care and beauty products.

Each hair originates in a germinative cell at the bottom of a hair follicle, a tube-like pocket in the scalp. The follicle directs the hair to the surface of the scalp. Each follicle has attached sebaceous glands. The oil produced by the sebaceous glands combines with other debris creates sebum, a substance that can form a plug, which blocks the opening of the hair follicle and traps the hair in the follicle. It is believed that accumulated sebum within the follicles and on the scalp surrounding the follicles is an important factor in hair loss and baldness.

Sebum cannot be dissolved and removed from the hair follicles and scalp by regular shampoos. Therefore, several hair care products have been developed to cleanse the sebum from the follicle opening and release the entrapped hair. Two of these products are Foli-Kleen™, Sable Laboratories, Pompano Beach, Fla., described in U.S. Pat. No. 5,610,071; and Nioxin™, Nioxin Research Laboratories, Inc., Lithia Springs, Ga.

The Foli-Kleen product contains both black cohosh extract and surfactants. The surfactants used in Foli-Kleen, sodium cocate, sulfonated vegetable oil and sulfonated castor oil, can cause scalp irritation and are not as effective in removing sebum as the preferred surfactants of the present invention. The Nioxin products do not contain either black cohosh extract or surfactants.

BRIEF SUMMARY OF THE INVENTION

The present invention provides new formulations that are uniquely effective in cleansing the scalp and follicle openings of sebum and allowing normal hair growth. These formulations are complex mixtures of botanical and herbal ingredients, including black cohosh extract, and the surfactants sodium $C_{14-16}$-olefin sulfonate, sodium lauryl sulfonate, and disodium laureth sulfosuccinate, It is an object of the present invention to provide new formulations for cleansing the scalp and hair follicle openings.

It is a further object of the present invention to provide a method for cleansing the scalp and hair follicle openings using the new formulations.

DETAILED DESCRIPTION OF THE INVENTION

Unlike previous shampoos and other hair care products, the formulations of the present invention contain a unique combination of black cohosh extract and surfactants that more effectively cleanse the scalp and hair follicle openings, thus allowing normal hair growth.

The formulations of the present invention are particularly effective in reducing hair loss and reducing the time necessary for hair re-growth in cancer patients who undergo chemotherapy. The American Hair Loss Council reports that adequate hair re-growth may take six months to one year after chemotherapy is complete. Chemotherapy patients who have used the formulations of the present invention, however, have re-grown their hair to the point where wigs are no longer necessary in as little as eight weeks. In addition, these patients did not have the usual dry itchy scalp following chemotherapy and their new hair was very soft.

The formulations of the present invention comprise black cohosh extract, certain surfactants and, optionally, other herbal and botanical extracts, conditioners, thickeners, and preservatives. Coloring agents and fragrances, preferably herbal fragrances, may be added to the formulation.

Black cohosh extract is a botanical known as an astringent, diuretic and expectorant. Black cohosh extract has been found to be particularly effective in cleansing the scalp and hair follicle openings to allow normal hair growth.

Surprisingly, it has been found that a group of surfactants, consisting of sodium $C_{14-16}$-olefin sulfonate, sodium lauryl sulfonate, disodium laureth sulfosuccinate, and combinations thereof, when used in combination with black cohosh extract are particularly effective in removing sebum from the scalp and hair follicle openings. These surfactants also are less irritating to the scalp than the prior art surfactants. Polysorbate 20 may be used as a surfactant for fragrances added to the formulation without detracting from the effectiveness of the above surfactants. Sodium cocate, sulfonated vegetable oil and sulfonated castor oil should be avoided because they may irritate the scalp and do not have the advantageous cleansing properties of the preferred surfactants.

Other herbs and botanicals that may be included in the formulations of the present invention are extracts of aloe vera, balm mint, burdock, chamomile, dong quai, fenugreek, hawthorn, hops, kelp, nettle, rosemary, sage, saw palmetto, yarrow, wild yam and witch hazel, and combinations thereof Preferred herbs and botanicals used with black cohosh in the present formulations are aloe vera, chamomile, dong quai, fenugreek, hawthorn, kelp, nettle, sage saw palmetto, wild yam and witch hazel.

Conditioners that may be used in the formulations of this invention are hydrolyzed collagen, lanolin, lecithin, panthenol and tocopherol acetate, and combinations thereof.

Preservatives suitable for the formulations of the present invention are methyl paraben, propyl paraben, phenoxy ethanol, and combinations thereof Formaldehyde releasing preservatives should be avoided.

Formulations of the present invention typically will comprise about 0.75–2.50 weight percent black cohosh extract, preferably about 0.85–1.70 weight percent; about 3.50–16.00 weight percent surfactants, preferably about 6.00–12.20 weight percent; about 0–9.00 weight percent other herbs and botanicals, preferably about 2.50–3.00 weight percent; about 0.25–7.50 weight percent conditioners, preferably about 0.90–3.00 weight percent; about 0.10–1.00 weight percent thickeners, preferably about 0.10–0.70 weight percent; about 10.00–18.00 weight percent isopropyl alcohol, preferably about 12.00–15.00 weight percent; about 50.00–75.00 weight percent water, preferably about 60.00–70.00 weight percent; and coloring agents, fragrances and preservatives as desired.

The formulations of the present invention can be formulated as liquids for direct application to the scalp. In a professional salon setting, the liquid formulation may be applied to the scalp with a soft bristle brush, gently rubbed on with the fingertips, or sprayed on through a spray cap on the formulation container. The formulations are left on the scalp and hair for an effective period of time, generally about 15 to 20 minutes, after which the scalp and hair may be shampooed and a hair conditioner applied. The formulation may be applied as frequently as desired.

For self-application by a user at home, the liquid formulation also may be applied as above. In this case, however, it is convenient to apply the formulation in the evening and leave it on the scalp overnight without shampooing. A second application of the formulation then may be made the next morning and left on for 15 to 20 minutes, after which the scalp and hair may be shampooed and a hair conditioner applied. The formulation may be applied as frequently as desired.

EXAMPLES

Example 1. Professional Formulation

In a first mixing vessel, 65.7 grams of deionized water was heated to 100 F. Polyethoxylated lanolin, 0.48 grams, was added and stirred until dissolved. 0.58 grams of xanthan gum was added to the mixing vessel and stirred until homogenous. Then 13.44 grams of isopropyl alcohol was added with stirring. Next 0.87 grams of black cohosh extract, 0.48 grams of witch hazel extract, 0.48 grams of chamomile extract, 0.48 grams of kelp extract, 0.48 grams of nettle extract, 0.48 grams of sage extract, 0.48 grams of aloe vera extract, 0.48 grams of hydrolyzed collagen, 0.48 grams of tocopherol acetate, and 0.48 grams of panthanol were added to the mixing vessel with stirring.

In a second mixing vessel, 2.67 grams of sodium $C_{14-16}$ olefin sulfonate, 9.44 grams of Stepan LCW (a sodium lauryl sulfoacetate and disodium laureth sulfosuccinate mixture from Stepan chemical Co.), and 0.48 grams of lecithin were added and stirred to homogeneity. This surfactant mixture then was added to the first mixing vessel with vigorous stirring.

Finally, 0.15 grams of methyl paraben, 0.10 grams of propyl paraben, and 0.08 grams of phenoxyethanol were added, and the formulation was brought to the desired color by adding about 0.08 grams of carmel coloring, also with stirring. The weight of the entire batch was brought to 100 grams by adding water. The final mixture was cooled and filled into bottles.

The formulation of example 1 was applied to the scalp of experimental subject Ms. Jo, a chemotherapy patient by a professional beautician using the method described above. At the time of the first application, Ms. Jo had lost all of her hair. The formulation of Example 1 was applied weekly for eight weeks, during which Ms. Jo continued having chemotherapy and radiation treatments. After eight weeks Ms. Jo had thick hair about three-fourths to one inch long over her entire scalp.

Example 2. Home Care Formulation

In a first mixing vessel, 68.2 grams of deionized water was heated to 100 F. Polyethoxylated lanolin, 0,92 grams, was added and stirred until dissolved. 0.14 grams of xanthan gum was added to the mixing vessel and stirred until homogenous. Then 13.8 grams of isopropyl alcohol was added with stirring. Next 1.60 grams of black cohosh extract, 0.92 grams of witch hazel extract, 0.92 grams of chamomile extract, and 0.92 grams of nettle extract were added to the mixing vessel with stirring.

In a second mixing vessel, 0.92 grams of sodium $C_{14-16}$ sulfonate, 4.82 grams of Stepan LCW, and 0.23 grams of lecithin were added and stirred to homogeneity. This surfactant mixture then was added to the first mixing vessel with vigorous stirring.

Next, 0.08 grams of herbal fragrance was added to 0.81 grams of polysorbate 20 with stirring. The fragrance and surfactant mixture then was added to the first mixing vessel and stirred. Finally, 0.15 grams of methyl paraben, 0.10 grams of propyl paraben, and 0.08 grams of phenoxyethanol were added, and the formulation was brought to the desired color by adding about 0.08 grams of carmel coloring, also with stirring. The weight of the entire batch was brought to 100 grams by adding water. The final mixture was cooled and filled into bottles.

The formulation of example 2 was applied by experimental subject Mr. Chris to his scalp at home, using the method described above. Mr. Chris applied the formulation to his scalp each evening and left it on his scalp over night. He then applied the formulation again the next morning and left it on his scalp for 15 to 20 minutes before shampooing. At the end of four weeks, the bald area on the crown of Mr. Chris' head was reduced by 15 percent and hair was filling in the remaining center portion of the area.

While the present invention has been described in terms of the preferred embodiments, it is recognized that persons skilled in this art will readily perceive many modifications and variations in the embodiments described above. Such modifications and variations are included within the scope of this invention.

I claim:

1. A formulation for cleansing the scalp and hair follicle openings, comprising black cohosh extract, and a surfactant selected from the group consisting of sodium $C_{14-16}$ olefin sulfonate, sodium lauryl sulfoacetate, disodium laureth sulfosuccinate and combinations thereof.

2. The formulation of claim 1, comprising about 0.75–2.50 weight percent of black cohosh extract.

3. The formulation of claim 2, comprising about 0.85–1.70 weight percent black cohosh extract.

4. The formulation of claim 1, comprising about 3.50–16.00 weight percent surfactants.

5. The formulation of claim 4, comprising about 6.00–12.20 weight percent surfactants.

6. The formulation of claim 1 including polysorbate 20 as an additional surfactant.

7. The formulation of claim 1 including isopropyl alcohol and water.

8. The formulation of claim 1 including one or more other herbs and botanicals, and/or one or more conditioners, and/or one or more thickeners, and/or one or more preservatives, and/or one or more coloring agents, and/or one or more fragrances, or combinations thereof.

9. The formulation of claim 8 wherein the other herb or botanical is aloe vera, chamomile, dong quai, fenugreek, hawthorn, kelp, nettle, sage, saw palmetto, wild yam or witch hazel or combinations thereof.

10. The formulation of claim 8 wherein the conditioner is lanolin, panthenol, tocopherol acetate, or combinations thereof.

11. The formulation of claim 8 wherein the thickener is xanthan gum.

12. A formulation for cleansing the scalp and hair follicle openings, comprising black cohosh extract, sodium $C_{14-16}$ olefin sulfonate, sodium lauryl sulfoacetate, disodium laureth sulfosuccinate, witch hazel extract, chamomile extract, kelp extract, nettle extract, sage extract, aloe vera extract, polyethoxylated lanolin, lecithin, and xanthan gum.

13. A formulation for cleansing the scalp and hair follicle openings, comprising black cohosh extract, sodium $C_{14-16}$ olefin sulfonate, sodium lauryl sulfoacetate, disodium laureth sulfosuccinate, polysorbate 20, witch hazel extract, chamomile extract, nettle extract, polyethoxylated lanolin, lecithin, xanthan gum and a fragrance.

14. A method for cleansing the scalp and hair follicle openings, comprising applying to the scalp a formulation comprising black cohosh extract and a surfactant selected from the group consisting of sodium $C_{14-16}$ olefin sulfonate, sodium lauryl sulfoacetate, disodium laureth sulfosuccinate and combinations thereof, and allowing the formulation to remain on the scalp for an effective period of time to clean the scalp and hair follicle openings.

* * * * *